United States Patent
Young

(10) Patent No.: US 8,679,068 B2
(45) Date of Patent: Mar. 25, 2014

(54) PRE-FILLED SYRINGE INCLUDING AN OXYGEN ABSORBER

(75) Inventor: Matthew Young, Over (GB)

(73) Assignee: Oval Medical Technologies Limited, Cambridge (GB)

( * ) Notice: Subject to any disclaimer, the term of this patent is extended or adjusted under 35 U.S.C. 154(b) by 212 days.

(21) Appl. No.: 13/383,239

(22) PCT Filed: Jun. 23, 2010

(86) PCT No.: PCT/GB2010/001244
§ 371 (c)(1),
(2), (4) Date: Feb. 3, 2012

(87) PCT Pub. No.: WO2011/004137
PCT Pub. Date: Jan. 13, 2011

(65) Prior Publication Data
US 2012/0143144 A1   Jun. 7, 2012

(30) Foreign Application Priority Data

Jul. 10, 2009  (GB) .................................. 0912073.4

(51) Int. Cl.
*A61M 5/31*   (2006.01)

(52) U.S. Cl.
USPC ........................... 604/187; 604/218; 206/439

(58) Field of Classification Search
USPC ........................... 604/187, 195, 218; 206/439
See application file for complete search history.

(56) References Cited

U.S. PATENT DOCUMENTS

| | | |
|---|---|---|
| 3,507,386 A | 4/1970 | Ishii |
| 3,682,174 A | 8/1972 | Cohen |
| 3,946,732 A | 3/1976 | Hurscham |
| 4,424,057 A | 1/1984 | House |
| 4,615,468 A | 10/1986 | Gay |
| 5,244,465 A | 9/1993 | Michel |
| 5,250,037 A | 10/1993 | Bitdinger |
| 5,354,286 A | 10/1994 | Mesa |
| 5,531,683 A | 7/1996 | Kriesel |
| 6,073,759 A | 6/2000 | Lamborne |
| 6,331,174 B1 | 12/2001 | Reinhard |
| 2002/0007149 A1 | 1/2002 | Nelson |
| 2003/0106824 A1* | 6/2003 | Wilmot et al. ................. 206/439 |
| 2008/0072992 A1* | 3/2008 | Baleriaux et al. ................. 141/5 |

FOREIGN PATENT DOCUMENTS

| | | |
|---|---|---|
| AU | 198811602 | 8/1989 |
| EP | 0458337 | 11/1991 |
| EP | 0473159 | 3/1992 |
| EP | 0665028 | 8/1995 |
| EP | 1679365 | 7/2006 |
| WO | WO-97/37628 | 10/1997 |
| WO | WO-00/71185 | 11/2000 |

OTHER PUBLICATIONS

United Kingdom Intellectual Property Office Search Report for GB0910934.9, Oct. 2009.

(Continued)

*Primary Examiner* — Laura Bouchelle
(74) *Attorney, Agent, or Firm* — Lando & Anastasi, LLP

(57) ABSTRACT

The invention provides a syringe or autoinjector for dispensing a drug comprising a rigid syringe body containing the drug, an oxygen absorbing material, a separating element between the drug and oxygen absorbing material to prevent the drug from contacting the oxygen absorbing material but which allows oxygen to pass from the drug to the oxygen absorbing material, and an oxygen impermeable container enclosing both the drug and the oxygen absorbing material, wherein the oxygen impermeable container partially or fully forms the rigid syringe body or is held within the rigid syringe body.

20 Claims, 9 Drawing Sheets

(56) References Cited

OTHER PUBLICATIONS

International Search Report for PCT/GB2010/001243, Aug. 2010.
United Kingdom Intellectual Property Office Search Report for GB0912073.4, Oct. 2009.
International Search Report for PCT/GB2010/001244, Oct. 2010.
International Preliminary Report on Patentability for PCT/GB2010/001243, Jan. 2012.
International Preliminary Report on Patentability for PCT/GB2010/001244, Jan. 2012.

* cited by examiner

PRE-FILLED SYRINGE INCLUDING AN OXYGEN ABSORBER

CROSS REFERENCE TO RELATED APPLICATION

This application is a U.S. National Stage patent application of PCT/GB2010/001244, which designated the United States, filed Jun. 23, 2010, entitled A Pre-Filled Syringe including an Oxygen Absorber, which claims priority to Great Britian Patent Application No. 0912073.4, filed Jul. 10, 2009, the disclosures of which are expressly incorporated herein by reference.

FIELD OF THE INVENTION

This invention relates to devices for drug storage and drug administration to a patient.

BACKGROUND TO THE INVENTION

One type of drug delivery device known in the art is an injection-apparatus which contains a medical, therapeutic, diagnostic, pharmaceutical or cosmetic compound (drug) before it is administered to a patient, and which is used to administer the compound through the skin of the patient via a hollow needle. Injection apparatus of this type includes pre-filled syringes and autoinjectors.

A pre-filled syringe is a syringe which is filled with drug prior to distribution to the end user who will administer the drug to the patient. A pre-filled syringe typically includes a drug containment container forming part of a syringe body, a plunger for expelling the drug, and either an attached hypodermic needle or else features to allow a needle to be attached by the user prior to administration of the drug so that the drug can be delivered directly from the syringe in which it is supplied through the needle into the patient. The user of the syringe will typically need to be trained in the skill of administering injections, and may be the patient themselves, a doctor, a nurse or other carer such as a family member.

Autoinjectors are syringes that are used to reduce the skill needed to administer an injection compared with an ordinary, non-automatic pre-filled syringe. They are therefore more suitable than ordinary syringes for use by people who have not been trained in the skill of giving injections, and are often used to administer drugs for treating unplanned 'crisis' conditions such as anaphylactic shock or nerve gas poisoning where trained medical personnel may not be available. They are also used where it is advantageous for drugs to be administered in a home environment without the presence of trained medical personnel, for instance in the delivery of some drugs for treating cancer or auto-immune diseases. In this instance the person administering the drug may be the patient themselves or a family member who may have disabilities including limited strength, dexterity or vision.

Autoinjectors typically include a drug containment container along with a secondary structure which includes mechanisms to automatically insert a hypodermic needle into the patient and operate the plunger to administer the drug. This drug containment container is generally filled with drug in an aseptic environment and then assembled to the secondary structure after it has left this aseptic environment. In this way the risk of particulate and biological contamination of the drug by exposure to the secondary structure is reduced. Examples of this type of device include the EpiPen™ from King Pharmaceuticals and the DAI™ from Scandinavian Health Limited.

In a similar way pre-filled syringes may be assembled to additional structures outside the sterile filling environment after filling, such as needle safety mechanisms to prevent cross-contamination of blood borne diseases due to needle stick injuries after use.

These types of syringes are usually made from glass because glass provides various benefits. Glass has good resistance to moisture and gas permeation.

It has good transparency which allows the drug to be inspected after filling. It is also relatively inert to many drugs. However glass has several disadvantages including fragility and the ability to contaminate certain drugs.

An alternative group of materials, cyclic olefin polymers, have been used instead of glass as they typically have less of a contaminating effect on drugs and still exhibit good transparency. These materials include cyclic olefin copolymers such as Topas™ from Topas Advanced Polymers GmbH, and cyclic olefin homopolymers such as Crystal Zenith™ from Daikyo. However these materials do not have the same resistance to gas permeability as glass so can allow greater permeation of atmospheric gases such as oxygen through the container into the drug, where the gases can cause the drug to degrade.

Oxygen absorbing materials are known to be used in food and beverage packaging to reduce the oxygen levels within packaging. Typical oxygen absorbing materials include iron, low molecular weight organic compounds such as ascorbic acid and sodium ascorbate, and polymeric materials incorporating a resin and a catalyst.

Patent application US 2008/0072992 describes a drug container which may be made of cyclic olefin copolymer, and which is enclosed within a foil pouch in which the atmosphere between the container and the envelope wall is exposed to an oxygen-absorbing material. US 2003/0106824 A1 also describes a sealed package containing a medicament container and a gas absorbing component.

Both of the above described patent applications require a user to first remove the sealed envelope in order to access the drug. This arrangement has various disadvantages when used with prefilled syringes and autoinjectors:

- it increases the number of steps needed for a user to administer the drug;
- the envelope can obscure the drug during storage of the syringes or autoinjector making the drug more difficult or impossible to inspect for quality prior to use;
- the envelope increases the size of the overall drug packaging;
- there is a risk that the user will remove the drug container prematurely from the envelope causing the drug to be contaminated by oxygen, particularly if the user is not aware of the function and importance of the envelope in protecting the drug from oxygen;
- users may find it difficult to open the envelope, particularly those users with physical or cognitive disabilities.

There are also other issues which need to be considered when oxygen absorbers are used in conjunction with syringes or autoinjectors. It is necessary to prevent oxygen absorbers from absorbing excessive oxygen before they are assembled into the syringe or autoinjector so that they do not lose their efficacy. The oxygen absorber may also be a source of particulate, chemical or biological contamination and so may need to be isolated from the drug and drug delivery path.

SUMMARY OF THE INVENTION

The present invention is defined in the appended claims, to which reference should now be made.

The present invention aims to address some or all of the disadvantages described above by providing a syringe or autoinjector which includes a drug containment container enclosed in an oxygen-impermeable enclosure along with an oxygen absorbing material, such that the drug can be both protected from damage by exposure to oxygen yet also be accessed for administration to a patient easily, effectively and safely. The invention can also be used to improve the ease and effectiveness with which the drug can be inspected for quality after it has been packaged with the oxygen-absorbing material, to avoid premature breaching of the oxygen-impermeable enclosure by the user, and also to reduce the size of the overall packaging.

The term "oxygen-impermeable" as used herein, means substantially oxygen impermeable, as all materials are to some degree oxygen permeable. The oxygen impermeable enclosures, materials and seals described herein prevent diffusion of oxygen from the external environment through to the drug. The shelf life of a prefilled syringe or autoinjector is dependent on the rate at which contaminants, which oxygen is for many drugs, diffuse into the drug. So the degree to which the oxygen impermeable enclosure must be impermeable depends on the required shelf life of the syringe (typically greater than one year), the particular drug in the syringe and the volume and surface area of the enclosure. The oxygen impermeable enclosure must be sufficiently impermeable at a range of temperatures, pressures and humidity levels. The presence of an oxygen absorber within the oxygen impermeable enclosure may increase shelf life and/or reduce the degree to which the gas impermeable enclosure must be impermeable. However, an oxygen absorber will be quickly exhausted and become ineffective if placed in a highly oxygen permeable enclosure.

The term "oxygen permeable" as used herein means unsuitable as an oxygen barrier and at least more oxygen permeable than the oxygen impermeable enclosure.

The invention provides these benefits by including an oxygen-impermeable enclosure containing the drug and also an oxygen absorbing material positioned so that oxygen from the drug can pass to the oxygen absorbing material, all within the syringe itself. The oxygen absorbing material may either be in the form of a separate component or may be incorporated into one of the other functional components of the syringe or autoinjector. The invention may also provide a mechanism which allows the user to easily breach the oxygen impermeable enclosure and deliver the drug through a hypodermic needle in the normal course of administering the drug into a patient. The oxygen impermeable enclosure and the mechanism which provides the means of allowing the user to easily breach the oxygen impermeable enclosure are contained within or form part of the substantially rigid structure of the syringe or autoinjector that is handled by the user in the act of administering the drug, so simplifying the administration process significantly.

In one embodiment of the invention the syringe or autoinjector includes an inner container in contact with the drug which is made from an oxygen-permeable rigid material such as a cyclic olefin polymer appropriate for contact with a drug. This inner container is enclosed within a separate secondary outer container which is made from an oxygen-impermeable rigid material such as Ethylene Vinyl Alcohol (EVOH) or polyamide. A plunger is included within the inner container in order to expel the drug, and a plunger mechanism is included to move the plunger relative to the inner container in order to force the drug out of the container and into the patient, typically through a hollow hypodermic needle. Where the aforementioned plunger forms a barrier between the drug and the oxygen absorbing material the plunger can be made from an oxygen-permeable material to allow the oxygen absorbing component to absorb oxygen from the space in which the drug is contained. The inner container has at least one opening which is closed by a first seal which includes a material such as a cyclic olefin polymer which is in contact with and which is compatible with the stored drug. The outer enclosure has at least one opening which is closed by a second seal which is substantially impermeable to atmospheric gases such as oxygen. This second seal may comprise a multi-laminate material including an oxygen-impermeable material such as aluminium, a fluorocarbon or a polyamide. An oxygen absorbing material is positioned within the oxygen-impermeable outer enclosure but not in contact with the drug. The operation of the plunger mechanism causes both the first seal and the second seal to be broken to allow the drug to be dispensed into the patient.

The aforementioned seals may be broken by being pierced, by manual removal of a sealing element, by operation of a mechanical valve or by some other method.

In another embodiment of the invention, there is a space within the oxygen impermeable container surrounding substantially the entire outer surface of the inner container and in which the oxygen absorbing material is located, so that any oxygen entering the oxygen impermeable enclosure is more likely to be absorbed by the oxygen absorbing material than the drug.

In another embodiment of the invention the design of the syringe or autoinjector provides an oxygen permeable barrier to biological and particulate contamination between the drug and the oxygen absorbing material such that the oxygen absorbing material can be added to the syringe or autoinjector once it has left an aseptic filling environment without risk to the drug of biological or particulate contamination

BRIEF DESCRIPTION OF THE DRAWINGS

Examples of the present invention will now be described with reference to the accompanying drawings, in which.

DETAILED DESCRIPTION

Figure 1:
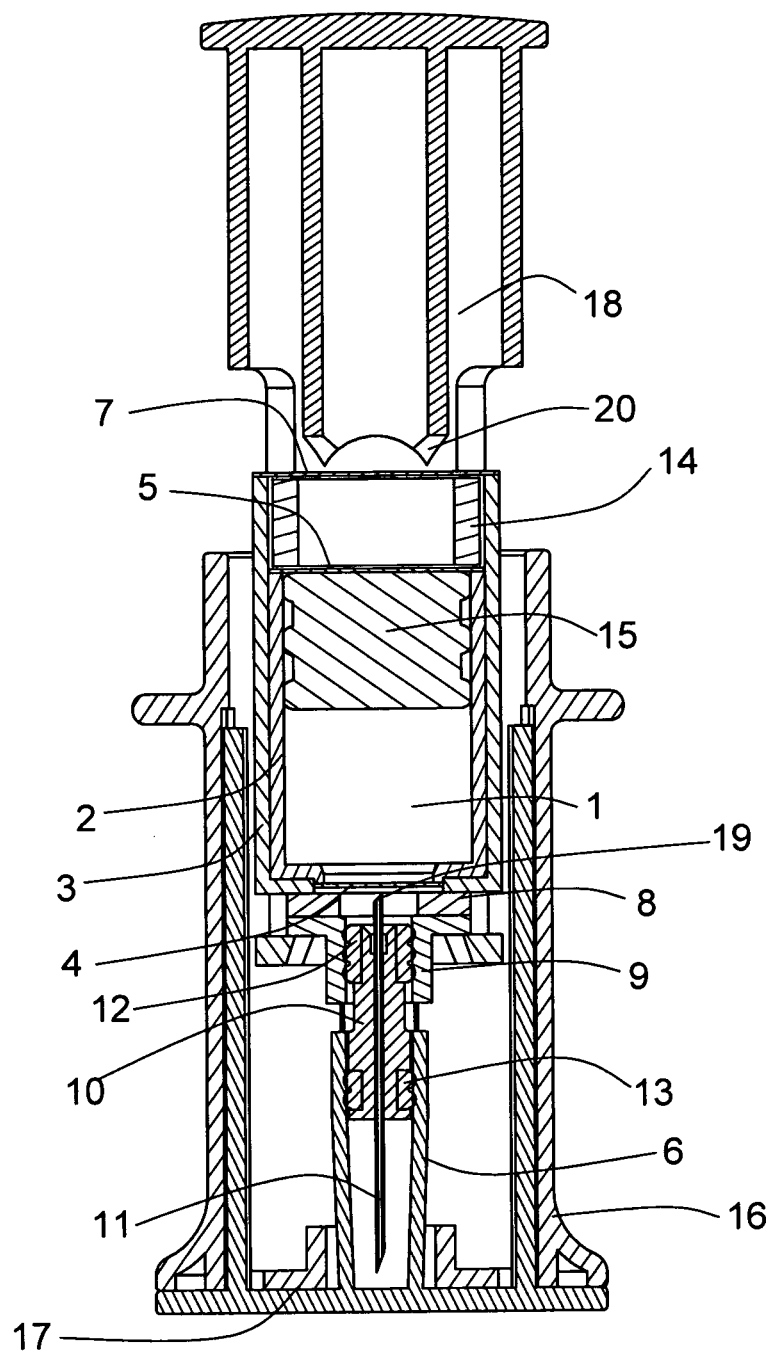
FIG. 1 is a longitudinal cross-section of an example of a syringe.

FIG. 1 shows a section view of a syringe embodying the present invention. The drug 1 is housed in a drug compatible inner container 2 which preferably includes a cyclic olefin polymer or other drug-compatible material in contact with the drug 1. The inner container is also preferably oxygen permeable. This is enclosed within an oxygen-impermeable outer container 3 made from a transparent oxygen-impermeable rigid material such as EVOH or polyamide.

The inner container 2 is sealed with a first oxygen-permeable seal 4 and a second oxygen-permeable seal 5 both of which preferably include a cyclic olefin polymer or other drug-compatible material in contact with the drug 1.

A oxygen-impermeable enclosure encloses the gas-permeable inner container 2, and is formed from the oxygen-impermeable outer container 3, an oxygen-impermeable needle cover 6, an oxygen-impermeable upper seal 7, an oxygen-impermeable elastomeric compression washer 8, an oxygen-impermeable compression washer retainer 9, a oxygen-impermeable needle-holding hub 10, which includes a hollow hypodermic needle 11, an oxygen-impermeable sealing feature 12, which seals the needle-holding hub 10 with the compression washer retainer 9, and a second oxygen-impermeable sealing feature 13 which seals the needle-holding hub 10 with the needle cover 6.

The outer container 3 includes an oxygen absorbing material 14 in a space between the second oxygen-permeable seal 5 and the oxygen-impermeable upper seal 7. An oxygen-permeable plunger 15 is positioned within the inner container 2. A rigid outer casing 16 encloses a substantial portion of the outer container 3.

In this embodiment, the oxygen absorbing material 14 is formed in a hollow cylindrical shape to allow a portion of a button 18 to pass through it and contact the plunger 15. However, the oxygen absorbing material may be formed in other shapes or in multiple parts and placed in different locations. An important requirement to prevent contamination of the drug is that that the oxygen absorbing material is not able to contact the drug at any point during manufacture, storage or dispensing. It is however in gaseous communication with the drug and held within the oxygen impermeable enclosure.

In order to administer the drug to the patient the user removes the manually removable needle shield 6, which forms part of the oxygen barrier as described for FIG. 1, and then applies the front of the syringe 17 to an appropriate area of the patient. The user then presses a button 18 which causes the inner oxygen permeable container 2 and outer oxygen impermeable container 3 to move axially towards the patient within the rigid outer casing 16, causing the front of the needle 11 to move forwards into the patient and the rear of the needle 19 to pierce the oxygen permeable seal 4. This movement of the button 18 also causes piercing details 20 to pierce the upper oxygen impermeable seal 7 and the second oxygen-permeable seal 5 and then cause the plunger 15 to be urged axially through the inner container 2 causing the drug to be urged through the needle 11 into the patient.

Figure 2:
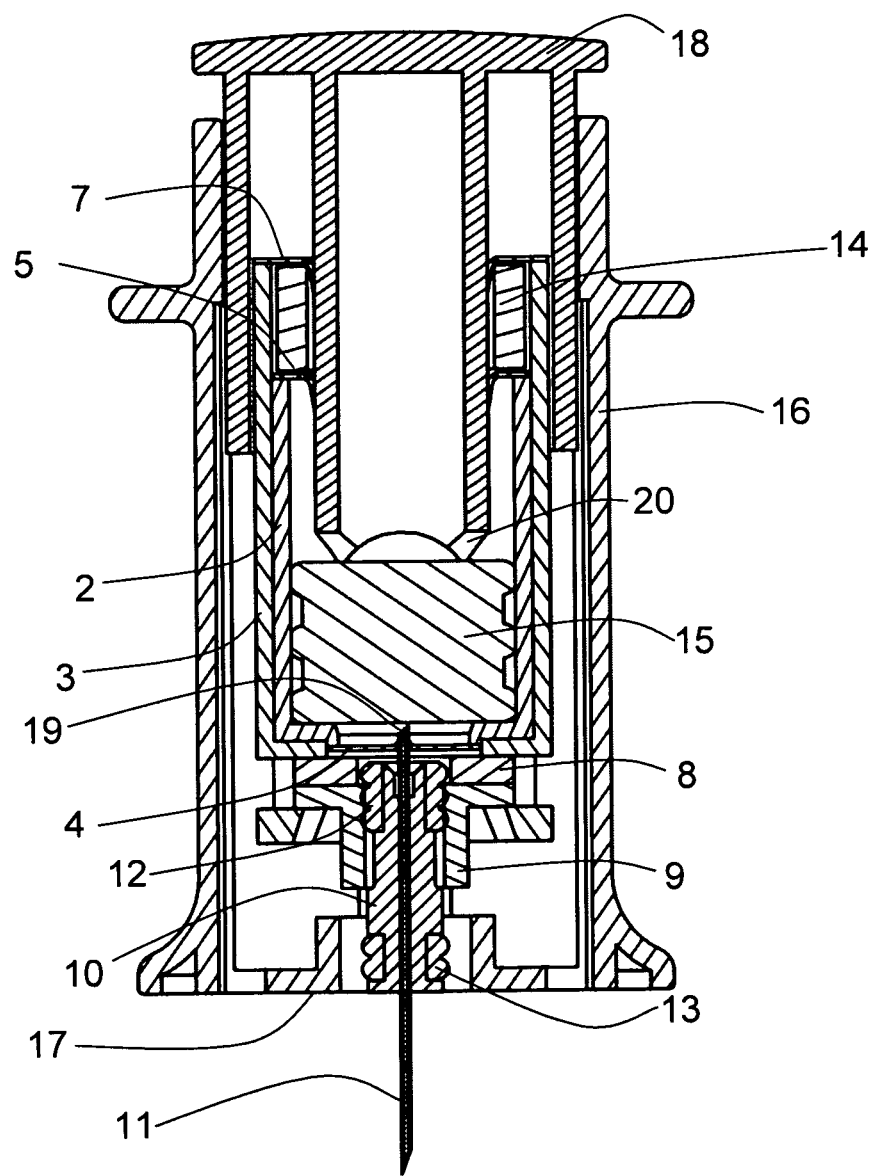
FIG. 2 is a longitudinal cross-section of the syringe of FIG. 1 at a point after the drug has been administered to a patient.

FIG. 2 shows the syringe of FIG. 1 at a point after the drug has been administered to the patient.

Figure 3:
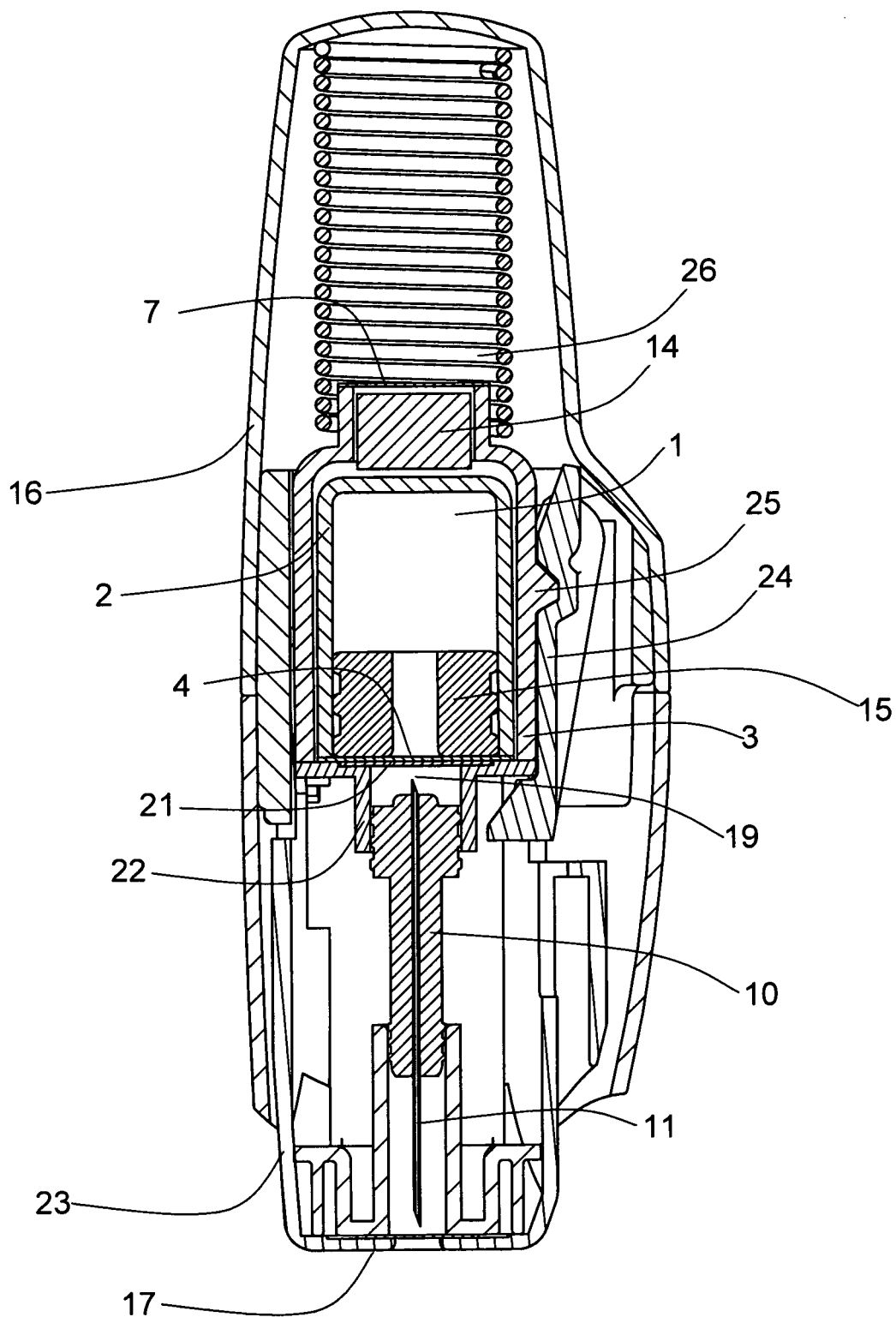
FIG. 3 is a longitudinal cross-section of an example of an autoinjector.

Preferred materials for the oxygen absorbing material 14 are iron, low molecular weight organic compounds such as ascorbic acid and sodium ascorbate, and polymeric materials incorporating a resin and a catalyst FIG. 3 shows a section view of an example of an autoinjector in accordance with the present invention. Like reference numerals have been used for components corresponding functionally to components in FIGS. 1 and 2. The drug 1 is housed in a oxygen-permeable inner container 2 which preferably includes a cyclic olefin polymer or other drug-compatible material in contact with the drug 1. This is enclosed within an oxygen-impermeable outer container 3 which preferably includes an oxygen-impermeable rigid material such as EVOH or polyamide. The inner container 2 is sealed with a first oxygen-permeable seal 4 which preferably includes a cyclic olefin polymer or other drug-compatible material in contact with the drug 1. The outer container 3 is sealed by an oxygen-impermeable second seal 21 in conjunction with an oxygen-impermeable retaining component 22.

An oxygen absorbing material 14 is positioned within the outer container 3. An oxygen-impermeable upper seal 7 seals an opening in the outer container 3 through which the oxygen absorbing material 14 can be assembled prior to the seal 7 being affixed in place.

Both the inner and outer containers are held within a rigid body which includes a rigid outer casing 16, needle shield 23, locking arm 24 and needle-holding hub 10.

In order to activate the autoinjector, the front of the autoinjector 17 is pressed onto the patient's skin, which causes the needle shield 23 to move, releasing a locking arm 24 which is engaged with an engaging detail 25 on the external surface of the outer container 3. This allows the locking arm 24 to disengage with the engaging detail 25, releasing a main drive spring 26. This main drive spring 26 is arranged so that it can drive the inner container 2 and outer container 3 axially through the autoinjector causing a hollow hypodermic needle 11 to be driven forward into the patient. The spring 26 also causes the first seal 4 and second seal 21 to be pierced by a piercing detail 19 on the back of the hollow hypodermic needle 11. The needle 11 is attached to the needle-holding hub 10 which continues to move relative to the inner container 2 after the seals 4 and 21 have been pierced due to the force of the spring 26. This in turn causes the plunger 15 to be driven axially through the inner container 2 expelling the drug 1 through the needle 11 and into the patient.

Figure 4:
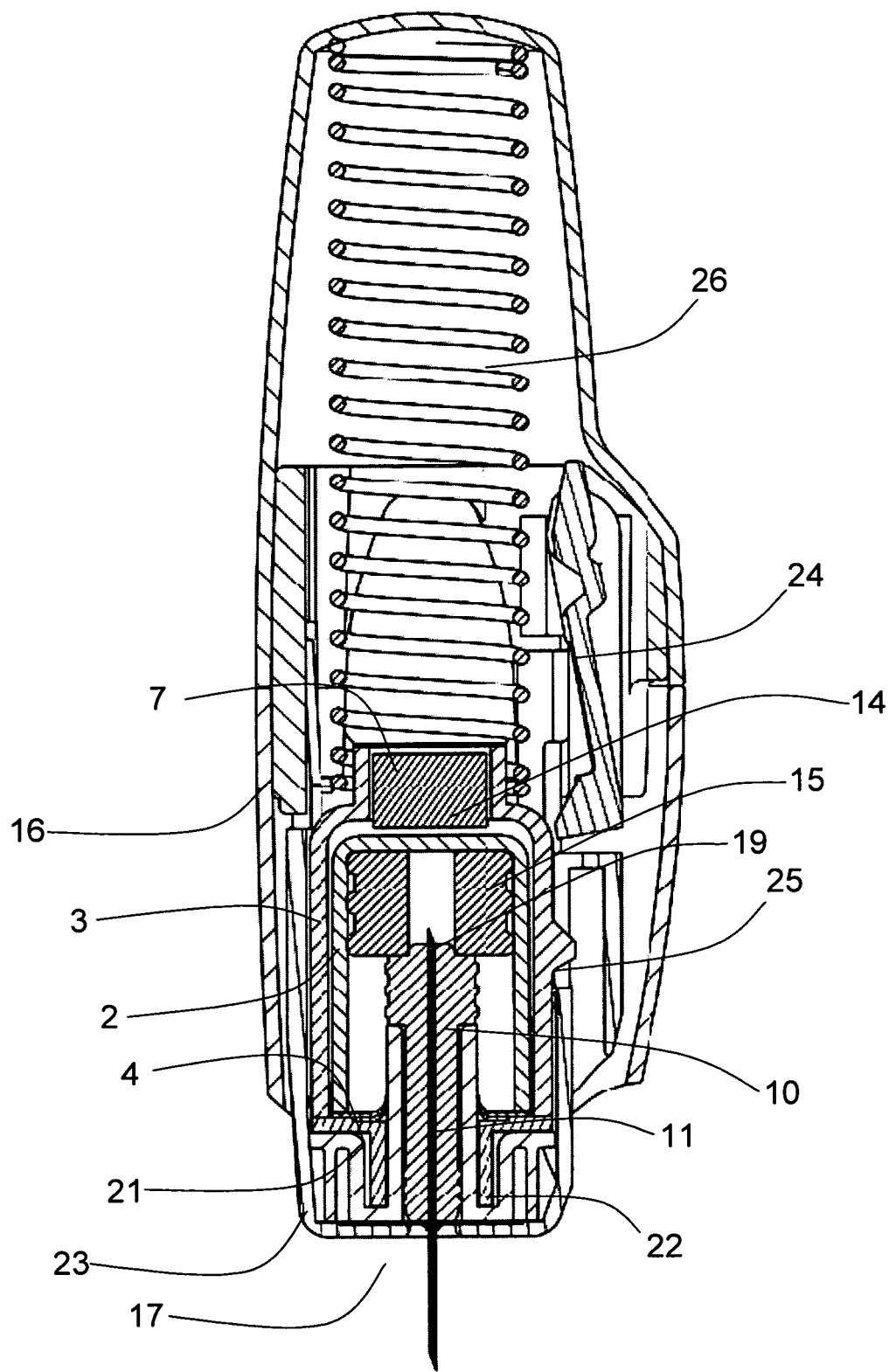
FIG. 4 is a longitudinal cross-section of the autoinjector of FIG. 3 at a point after the drug has been administered to a patient.

FIG. 4 shows a section view of the autoinjector of FIG. 3 at a point after the drug has been administered to the patient. The plunger 15 has moved relative to the inner container 2 to expel the drug 1 through the needle 11. The first seal 4 and second seal 21 have been broken by the needle 11 and the needle holding hub 10.

Figure 5:
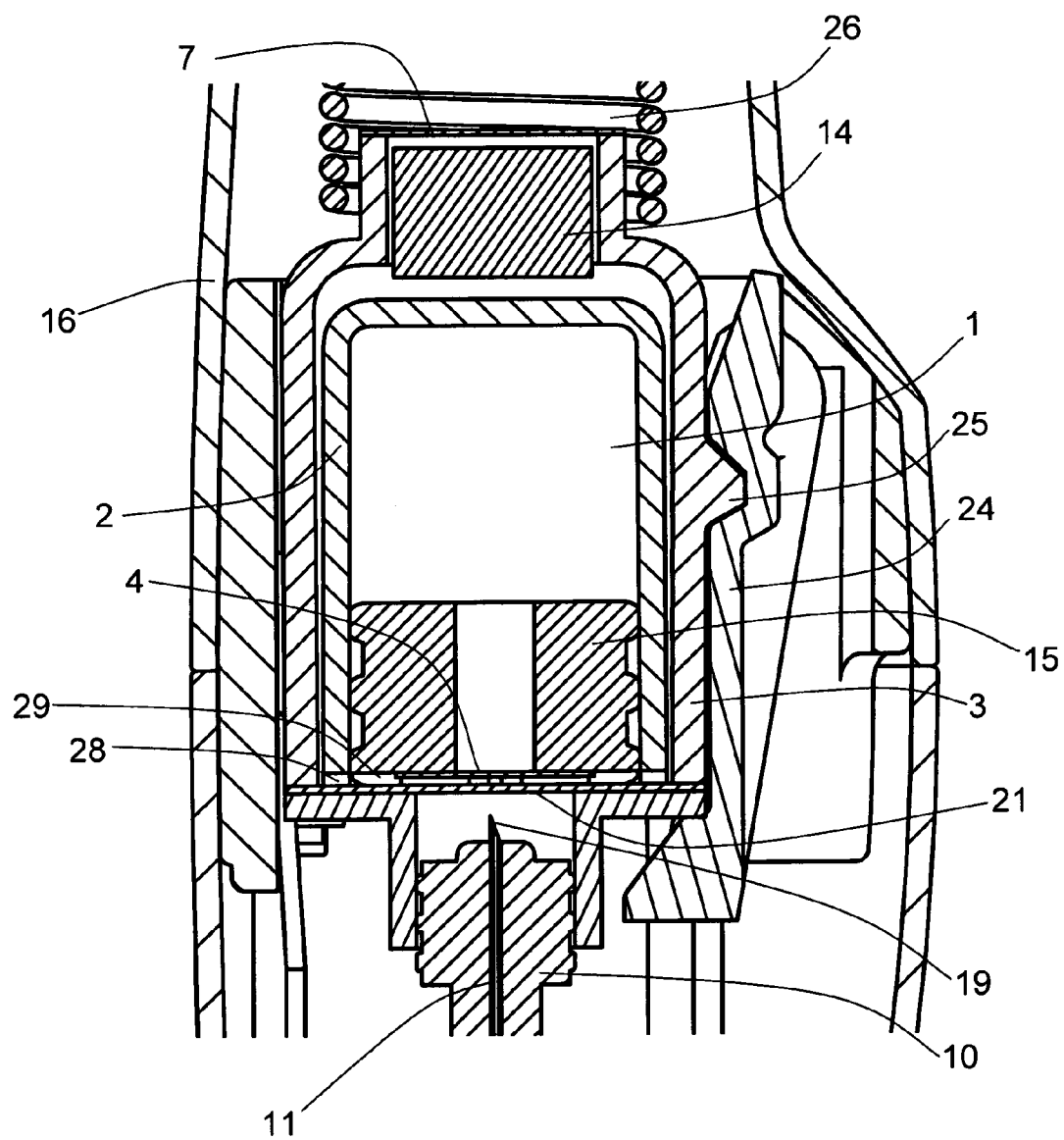
FIG. 5 is a longitudinal cross-section of an alternative example of the autoinjector of FIGS. 3 and 4 whereby the oxygen absorber is in gaseous communication with substantially the entire outer surface of the inner container.

FIG. 5 shows a partial section view of an alternative design of autoinjector that is substantially identical to that described in FIGS. 3 and 4 other than as follows (like reference numerals have been used for components corresponding functionally to components in FIGS. 3 and 4):

The oxygen-impermeable second seal 21 completely seals an opening in the oxygen-impermeable outer container 3;

The first oxygen-permeable seal 4 is sealed to the plunger 15;

The plunger 15 includes one or more passageways or surface grooves 29 to allow oxygen to move freely in a space situated between the plunger 15 and the oxygen-impermeable second seal 21; and One or more openings 28 are formed in the oxygen-permeable inner container 2 so that oxygen can pass freely from the space situated between the plunger 15 and the oxygen-impermeable second seal 21 around the outside of the oxygen-permeable inner container 2 to the oxygen absorbing material 14.

The above features cause the drug 1 to be substantially surrounded by a substantially oxygen-free gas-filled space which is in gaseous communication with the oxygen absorbing material 14, increasing the likelihood that any oxygen that does enter the oxygen-impermeable enclosure described above is absorbed by the oxygen absorbing material 14 rather than contaminating the drug 1.

It will be obvious to those skilled in the art that the designs described above in FIGS. 1 to 5 can be implemented in different ways. For instance, the seal 4 could be pierced by a component other than the needle such as the needle holding hub 10.

Figure 6A:
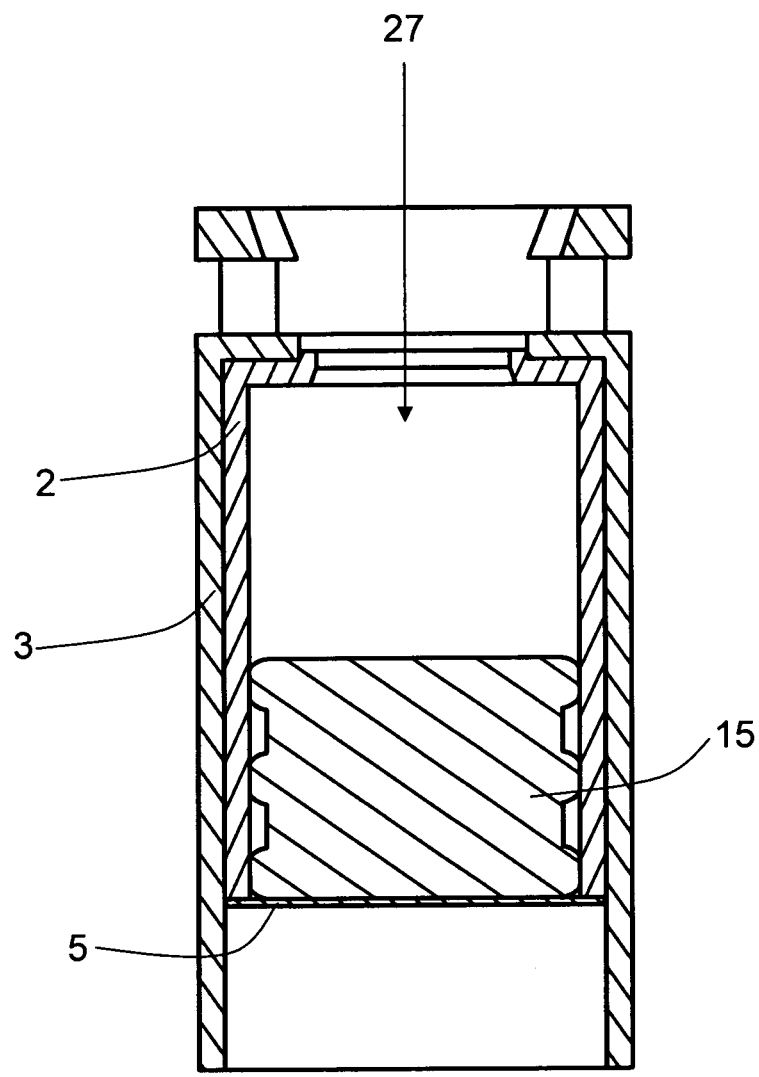
FIGS. 6a, 6b and 6c are longitudinal cross-section views of separate first and second parts of the syringe of FIGS. 1 and 2 showing a process for filling the first part with drug, sealing it with the second part, and adding an oxygen absorbing material.
Figure 6B:
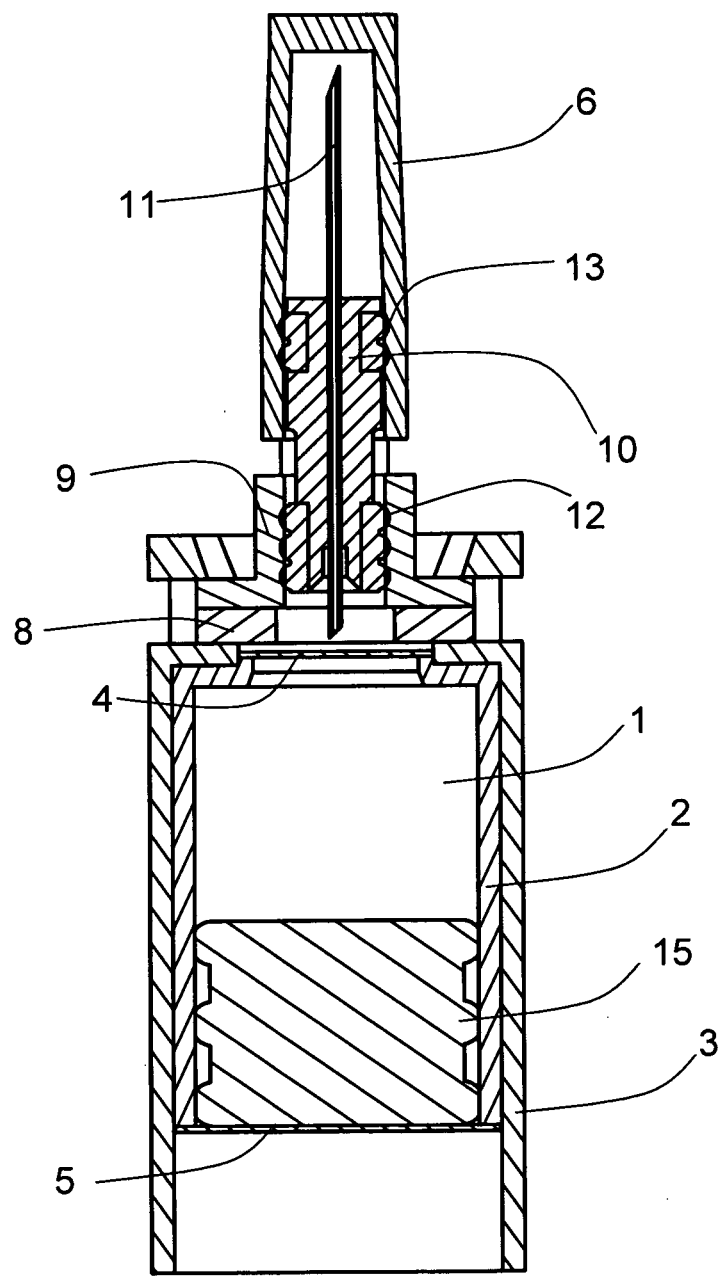
Figure 6C:
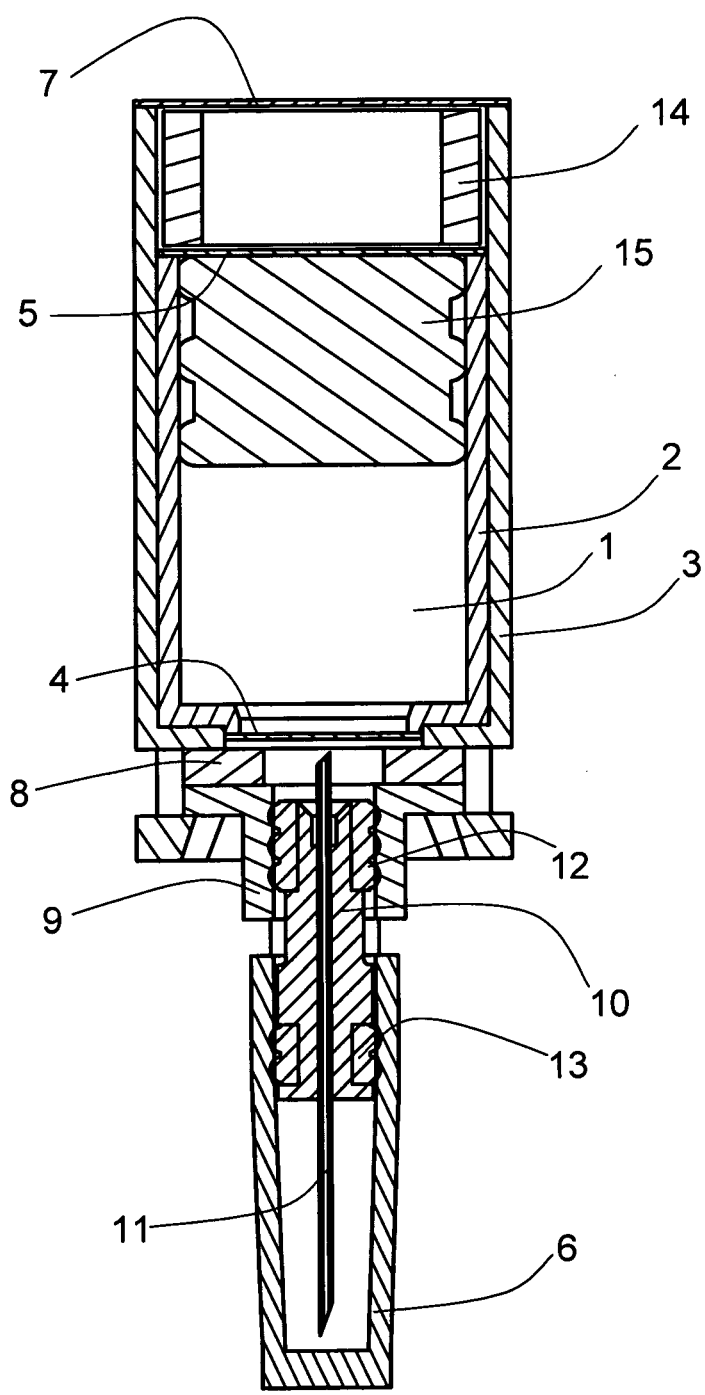

FIGS. 6a-6c show section views of an example of how the syringe of FIGS. 1 and 2 may be filled with drug and an oxygen absorbing material assembled to it according to the invention. Reference numerals corresponding to those in earlier Figures have been used again.

FIG. 6a shows a section view of a separate first part of the syringe prior filling or addition of an oxygen absorbing material. This part can be filled with drug and sealed with a second part of the syringe within a filling environment such as an aseptic or low particulate environment.

In this embodiment the separate part first comprises a oxygen-permeable, drug compatible inner container 2, an oxygen-impermeable outer container 3, a second oxygen-permeable seal 5 and an oxygen-permeable plunger 15. However it will be obvious to those skilled in the art that outer container 3 might alternatively not be included in this sub-assembly at this stage of the manufacturing process, and other embodiments of the invention such as that shown in the autoinjector of FIGS. 3 and 4 might not require a second oxygen-permeable seal 15 to be included. The arrow 27 indicates the opening through which the drug is filled into the inner container 2.

FIG. 6b shows a section view of the assembly of the aforementioned first and second parts of the syringe after the first part has been filled with drug and sealed by the second part. In this condition both the needle and the drug are protected from biological and particulate contamination so the assembly can safely leave the filling environment and enter a more contaminating environment without risk to the drug or needle of this type of contamination.

The drug 1 has been sealed into the first part by the addition of a second part which comprises a sub-assembly of: a first oxygen-permeable seal 4, an oxygen-impermeable needle cover 6, an oxygen-impermeable elastomeric compression washer 8, an oxygen-impermeable compression washer retainer 9, an oxygen-impermeable needle-holding hub 10, which includes a needle 11, an oxygen-impermeable sealing feature 12 which seals the needle-holding hub 10 with the compression washer retainer 9, and a second oxygen-impermeable sealing feature 13 which seals the needle-holding hub 10 with the needle cover 6.

FIG. 6c shows a section view of the part after it has had an oxygen absorbing material 14 added and an oxygen-impermeable seal 7 attached to the opening in the oxygen-impermeable outer container 3 through which the oxygen absorbing material 14 has been assembled, such that a complete oxygen-impermeable enclosure is created as described for the syringe of FIGS. 1 and 2 above. These later stages of adding the aforementioned oxygen absorbing material 14 and seal 7 do not need to be completed in the aseptic, low particulate or other filling environment in which the drug 1 was filled to the inner container 2, because the second oxygen-permeable seal 5 provides a barrier to protect the drug 1 from biological and particulate contamination as described above.

The subassembly of FIG. 6c can also be assembled to the rest of a syringe or autoinjector outside the filling environment for the same reason that the drug is protected from biological and particulate contamination. As the drug is also protected from oxygen by the oxygen absorbing material and oxygen-impermeable enclosure, it does not have to be assembled to the syringe or autoinjector at substantially the same time as the filling of the drug takes place but can be stored separately and assembled to the syringe or autoinjector closer to the time when it is needed.

Those skilled in the art would appreciate that the designs described above in

FIGS. 1 to 5 can be implemented in different ways. For instance, the inner container 2 and outer container 3 can be comoulded together or manufactured as separate components. The positions of the plunger and the various aforementioned seals can be varied. Seal 5 could be omitted so that the plunger 15 alone provides an oxygen-permeable barrier between the drug 1 and the oxygen absorber 14. The drug could be filled through the other end of the inner container 2 before the plunger is present, so that addition of the plunger after filling seals the drug into the aforementioned first part.

Although not specifically illustrated here it is envisaged that any of the seals described above could be sealed to the appropriate component by any of a number of possible different means known to those skilled in the art. These means include heat welding, induction welding, laser welding, ultrasonic welding, spin welding, hot plate welding, use of an adhesive including ultraviolet light curing adhesive, and use of a separate retaining component with or without an additional elastomeric compression component where the separate retaining component is itself screwed, snapped or welded to the appropriate container.

Figure 7:
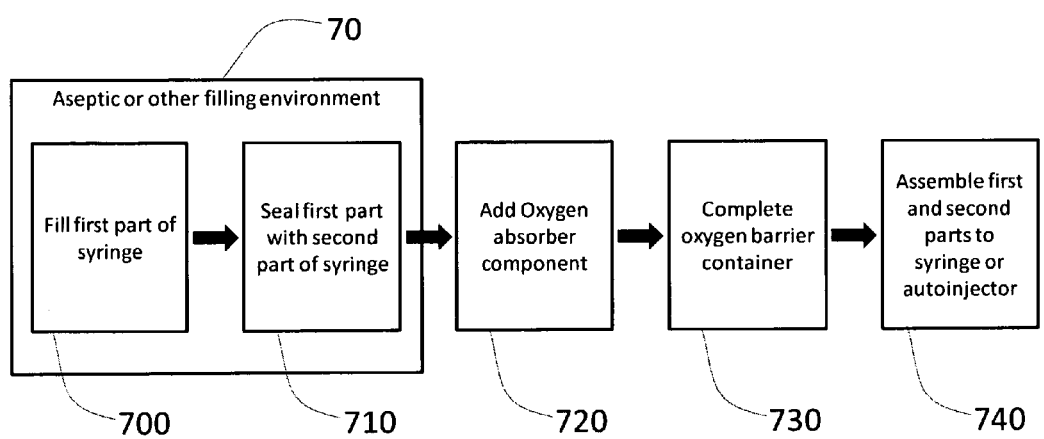
FIG. 7 is a schematic representation of a filling process which is applicable to the syringe of FIGS. 1, 2 and 5.

FIG. 7 shows a schematic representation of one process for filling a syringe or autoinjector that is applicable to the current invention, illustrating those steps performed in an aseptic filling environment and those steps that can be performed outside the aseptic filling environment. As described, a first part of the syringe is provided and filled with a dose of drug in step 700. This filled first part is then sealed by a second part of the syringe at step 710, to protect it from biological and particulate contamination. Steps 700 and 710 are performed within an aseptic or low particulate environment 70, which may be provided by a clean laminar air flow, as is known in the art.

In step 720, an oxygen absorber is added to the joined first and second parts. In step 730, an oxygen impermeable enclosure is formed around the oxygen absorber and the drug. Finally, in step 740, the oxygen impermeable enclosure is incorporated into the remainder of the syringe or autoinjector assembly.

The invention claimed is:
1. A syringe for dispensing a drug, comprising:
   a rigid syringe body containing the drug;
   an oxygen absorbing material,
   a separating element positioned between the drug and the oxygen absorbing material, the separating element preventing the drug from contacting oxygen absorbing material but allowing oxygen to pass from the drug to the oxygen absorbing material; and
   an oxygen impermeable enclosure enclosing both the drug and the oxygen absorbing material, wherein the oxygen impermeable enclosure partially or fully forms the rigid syringe body or is held within the rigid syringe body.

2. A syringe according to claim 1, wherein the oxygen impermeable enclosure is entirely within an outer surface of the rigid syringe body.

3. A syringe according to claim 1, further comprising an inner container in contact with and enclosing the drug, wherein the inner container has greater oxygen permeability than the oxygen impermeable enclosure.

4. A syringe according to claim 3, wherein the inner container is the separating element.

5. A syringe according to claim 4, wherein the oxygen absorbing material is in gaseous communication with substantially the entire outer surface of the inner container.

6. A syringe according claim 3, further comprising a plunger enclosed within the inner container.

7. A syringe according to claim 6, wherein the oxygen absorbing material is positioned on an opposite side of the drug to the plunger.

8. A syringe according to claim 3, wherein the inner container comprises cyclic olefin polymer material.

9. A syringe according to claim 1, wherein the syringe is an autoinjector.

10. A syringe according to claim 1, further comprising a needle through which the drug is dispensed from the syringe, wherein the needle is stored outside the oxygen impermeable enclosure prior to dispensing of the drug.

11. A syringe according to claim 1, further comprising a needle through which the drug is dispensed from the syringe, wherein the needle is stored inside the oxygen impermeable enclosure prior to dispensing of the drug.

12. A syringe according to claim 1, wherein the oxygen absorbing material is positioned on an opposite side of the drug to the needle.

13. A syringe according to claim 1, further comprising a breaching mechanism forming part of the rigid syringe body, wherein the breaching mechanism includes a user actuated element and is configured on actuation of the user actuated element to breach the oxygen impermeable enclosure to allow the drug to be dispensed from the syringe.

14. A syringe according to claim 13, wherein the breaching mechanism is configured so that operation of the breaching mechanism causes the drug to be dispensed from the syringe.

15. A syringe according to claim 13, further comprising a needle through which the drug is dispensed from the syringe, wherein the breaching mechanism is configured so that operation of the breaching mechanism puts the needle in fluid communication with the drug.

16. A syringe according to claim 13, wherein the oxygen absorbing material is shaped to allow the passage of a part of the breaching mechanism therethrough.

17. A syringe according to claim 13, wherein the oxygen impermeable enclosure includes an oxygen impermeable seal, wherein the breaching mechanism is configured to breach the seal on actuation of the user actuated element.

18. A syringe according to claim 17, wherein the oxygen-impermeable seal comprises aluminium, a polyamide, a fluorocarbon or Ethylene Vinyl Alcohol.

19. A method of manufacturing a syringe comprising a rigid syringe body, an inner container enclosing a drug, an oxygen absorbing material, the inner container preventing the oxygen absorbing material from contacting the drug but allowing oxygen to pass from the drug to the oxygen absorbing material, and an oxygen impermeable enclosure enclosing both the inner container and the oxygen absorbing material, wherein the oxygen impermeable enclosure partially or fully forms the rigid syringe body or is held within the rigid syringe body, comprising the steps of:

filling the inner container with the drug and sealing the inner container in an aseptic or low particulate environment, placing the oxygen absorbing material and the inner container into the oxygen impermeable enclosure in a different environment which is isolated from the first environment, and sealing the oxygen impermeable enclosure.

20. A method according to claim 19, wherein the oxygen absorbing material is placed in the oxygen impermeable enclosure after the filled and sealed inner container.

* * * * *